United States Patent [19]

Chapman et al.

[11] 4,225,740
[45] Sep. 30, 1980

[54] ALKYLATION SEPARATION PROCESS

[75] Inventors: Charles C. Chapman; Paul D. Hann, both of Bartlesville, Okla.

[73] Assignee: Phillips Petroleum Company, Bartlesville, Okla.

[21] Appl. No.: 39,931

[22] Filed: May 17, 1979

[51] Int. Cl.² .............................................. C07C 3/54
[52] U.S. Cl. .................................... 585/719; 585/723
[58] Field of Search ....................... 585/719, 712, 723

[56] References Cited

U.S. PATENT DOCUMENTS

| 2,392,962 | 1/1946  | Abrams et al. | 585/723 |
| 2,416,395 | 2/1947  | Kuhn, Jr.     | 585/723 |
| 2,431,500 | 11/1947 | Penick        | 585/723 |
| 3,925,501 | 12/1975 | Putney et al. | 585/719 |
| 4,059,649 | 11/1977 | Chapman et al.| 585/719 |
| 4,144,281 | 3/1979  | Chapman et al.| 585/719 |

Primary Examiner—George Crasanakis

[57] ABSTRACT

A process is provided for the alkylation of isoparaffins with olefins in the presence of an HF acid catalyst comprising separating a liquid hydrocarbon phase from the alkylation effluent, subjecting the hydrocarbon phase to HF stripping, separating the stripped hydrocarbon into a liquid and a vapor phase, fractionating the liquid phase into product streams, and pressurizing the vaporous stream prior to separation of $C_3$ and lighter materials. The HF alkylation process utilizes indirect heat exchange of various streams and compression of HF-free vapors.

8 Claims, 1 Drawing Figure

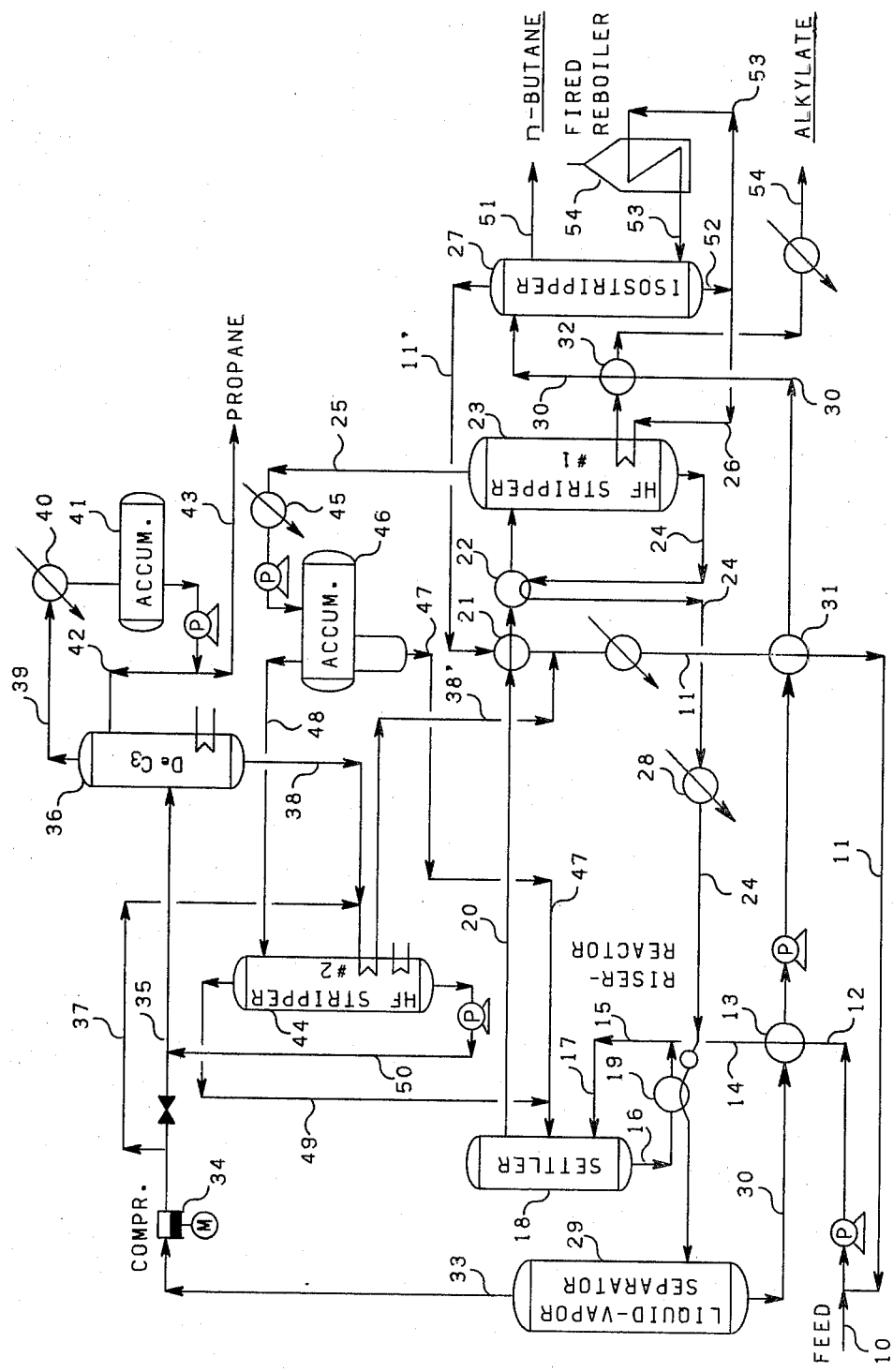

ALKYLATION SEPARATION PROCESS

SUMMARY OF THE INVENTION

According to the invention, a process is provided for alkylation of at least one isoparaffin and at least one olefin in the presence of an acid catalyst, separating the alkylation effluent into a liquid acid phase and a liquid hydrocarbon phase containing residual acid, stripping HF from the liquid hydrocarbon phase leaving substantially HF-free liquid hydrocarbon, subjecting the liquid hydrocarbon to heat exchange and separating same into a liquid and vapor fraction, fractionating the liquid fraction into product and recycle streams, pressurizing the vaporous stream and fractionating the pressurized stream into $C_3$ and lighter components and a recycle stream.

In accordance with another aspect of the invention, the HF alkylation process utilizes indirect heat exchange of various streams including compression of HF-free vapors. Liquid HF recycle catalyst is indirectly chilled by (1) flashing a portion of the HF-free liquid from the first HF stripper to which is charged the total HF alkylation hydrocarbon effluent. HF-containing vapors from this first HF-stripper are condensed, pumped to high pressure, and, after liquid HF removal therefrom by phase separation, are charged to the second HF-stripper, operated so that bottoms therefrom are HF-free. These bottoms are charged to the HF-free depropanizer. The flashed stream (1) is sent to liquid-vapor separation (2), and the recovered vapors, being HF-free, are compressed and charged also to the HF-free depropanizer. Bottoms from (2), used to indirectly precool the feed and isobutane recycled to alkylation, are charged to the isobutane stripper.

This invention is a process for low temperature HF alkylation of isobutane, propylene and butylenes mixed feed as from catalytic cracking or for predominantly butylenes feed. It is also advantageously used in areas where cooling water is relatively high temperature.

BRIEF DESCRIPTION OF THE DRAWING

Referring to the drawing, feed isobutane and feed olefin in line 10 plus HF-free recycle isobutane introduced by line 11 are passed by line 12 through heat exchanger 13 to cool stream 12, and the cooled stream is removed in line 14 and introduced into riser-reactor 15 along with recycle acid catalyst introduced by line 16. The reaction mass removed from riser-reactor 15 by way of line 17 and introduced into settler 18 wherein the reaction effluent is separated into an upper liquid hydrocarbon phase and a lower liquid HF acid phase. The HF acid phase is removed from settler 18 by line 16, passed through heat exchanger 19 to cool the HF phase and the cooled phase is returned to riser-reactor 15.

The upper hydrocarbon phase containing residual amounts of HF is removed from settler 18 by way of line 20, and stream 20 is heated by passage through heat exchanger 21 and 22 and then introduced into HF stripper 23 wherein the liquid hydrocarbon phase is subjected to conditions sufficient to remove HF and lighter hydrocarbons overhead by line 25 and HF-free hydrocarbons as bottoms in line 24. The hydrocarbon phase introduced into stripper 23 is preheated by indirect heat exchange in heat exchangers 21 and 22. HF stripper 23 is reboiled indirectly by hydrocarbons introduced by line 26, removed from the bottoms of isostripper 27. In HF stripper 23, all of the HF acid is removed overhead in stream 25 with most of the propane and enough isobutane to allow condensing with cooling water.

The bottoms 24 removed from HF stripper 23, free of HF, is cooled by passage through heat exchanger 22 and cooler 28 to heat exchanger 19 and then flashed and passed to liquid vapor separator 29. Liquid bottoms stream 30, removed from separator 29, is used to cool alkylation feed 12 in heat exchanger 13 and then is heated in heat exchanger 31 by recycled isobutane in line 11 and after heat exchanged in heat exchanger 32 with used reboiled fluid 26 from HF stripper 23 is charged to the isostripper 27 by line 30.

Vapors removed from separator 29 by way of line 33, which vapors are HF-free and comprise propane and isobutane, are passed to compressor 34 which can process only HF-free vapor and charged by way of line 35 to depropanizer 36. If desired, e.g., when low propylene (low propane) in feed to alkylation, a portion of the compressed vapors can by-pass depropanizer 36 by being introduced into line 37 and combined with the bottoms from depropanizer 36 in line 38 and returned as recycled isobutane to the reaction by way of line 11.

Overhead from depropanizer 36 in line 39 is condensed in cooler 40 and returned to accumulator 41. Propane is withdrawn from the accumulator and part returned by line 42 as reflux to depropanizer 36 and the remainder passed as product by line 43 for further use as desired.

Bottoms comprising isobutane removed by line 38 from fractionation 36 is passed as a source of heat for HF stripper 44 and then passed via 38' after combining with line 11 for recycle to the alkylation process.

Vapors comprising HF and light hydrocarbons including propane and isobutane, removed by line 25 from stripper 23, are passed to condenser 45 and the resulting liquid is pumped (to increase its pressure) into accumulator 46 wherein the stream is separated into two liquid phases: a lower liquid fraction comprising HF acid removed via line 47 and returned to settler 18, and an upper hydrocarbon phase, removed by line 48 and is passed to HF stripper 44 wherein it is subjected to stripping conditions sufficient to remove HF overhead by line 49 which is returned to settler 18. The bottoms stream 50, comprising isobutane and propane, is pumped to depropanizer 36 by way of line 35, downstream from compressor 34.

Isostripper 27 is operated under conditions such that isobutane vapor is removed overhead by line 11' and 11 and normal butane vapor is removed by line 51. Alkylate liquid product is removed as bottoms from stripper 27 by line 52 with part being passed by line 53 through reboiler 54 to supply heat and stripping vapors for lower portion of isostripper 27. Another portion of the alkylate bottoms is passed by line 26 and used to reboil stripper 23 to preheat isostripper feed 30 at 32, and then is removed as product by line 54.

In the process, the isoparaffin to olefin mol ratio in reactor 15 can vary considerably, but it generally is in the range of from about 2:1 up to about 25:1, usually from about 4:1 to about 15:1. The total hydrocarbon to HF catalyst volume ratio can vary considerably depending on the specific system, but the usual range is from about 1:10 to about 10:1. The HF alkylation reaction can be carried out in a wide temperature range usually in the range from about 0° F. ($-18°$ C.) to about 150° F. (66° C.) and at a pressure sufficient to maintain liquid phase conditions. The lower the reaction temperature, the higher the octane number of the butylenes alkylate. Since it is less expensive to use cooling water, the normal reaction zone temperature is about 90° F. (32° C.). In some areas cooling water is not of sufficiently low temperature and additional cooling of the alkylation reactants is required, as by heat exchanger 19 using flashed liquid hydrocarbons.

Any isoparaffin alone or in admixture with another isoparaffin is suitable for use with the present invention including isobutane, isopentane and isohexanes. Among olefins that can be used are propylene, butylenes, amylenes and many others alone or in admixture with other olefins. The invention is particularly suitable for the process and alkylation of isobutane with propylene and butylenes.

The HF stripper 23, utilized to strip HF from a liquid hydrocarbon phase separated from the alkylation effluent, is operated under conditions, temperature and pressure such that HF vapor and lighter hydrocarbon vapors are taken overhead and a liquid hydrocarbon stream substantially free of HF as bottoms. Usually the temperature in the upper portion of the stripper will be in the range of about 110° F. to about 130° F., the bottom temperature in the range of about 160° F. to about 180° F., and a pressure of about 100 psig to about 150 psig.

The isostripper 27 will be operated at conditions of relatively low pressure to separate isobutane vapor overhead and alkylate liquid as product with normal butane vapor as a side stream. This would usually require a top temperature in the range of about 130° F. to about 150° F., with a bottom temperature in the range of about 310° F. to about 340° F. and a pressure in the range of about 100 psig to about 130 psig.

Depropanizer 36 is operated under conditions to take propane vapor overhead and isobutane liquid as bottoms usually at a top temperature of about 115° F. to about 140° F. and a bottom temperature of about 190° F. to about 215° F. and a pressure in the range of about 220 psig to about 275 psig will be used.

HF stripper 44 will be operated under conditions to take overhead as vapor substantially all of the HF remaining in the feed to the stripper and liquid isobutane as bottoms which can contain some propane and will be operated under a top temperature in the range of about 110° F. to about 140° F., a bottom temperature in the range of about 160° F. to about 190° F. and a pressure in the range of about 175 psig to about 225 psig.

SPECIFIC EXAMPLE

Using the process of the invention shown in the drawing, the following flow rates and the following operating conditions in specific components of the system were calculated.

| | Calculated Example (Typical) | | |
|---|---|---|---|
| Operating Conditions | | Pressure (psig) | Temperature (°F.) |
| (29) | Liquid-Vapor Separator | 20 | 50 |
| (15) | HF Alkylation Zone: | 150 | 100 |
| | Isobutane/olefin mole ratio, 12:1 | | |
| | HF/total H/C vol. ratio, 4:1 | | |
| | Reactor residence, min., 0.5 | | |
| | Catalyst: | | |
| | Wt. % HF, 88 | | |
| | Wt. % H$_2$O, 2 | | |

| | Calculated Example (Typical) | | |
|---|---|---|---|
| | | Pressure | Temperature |
| | Wt. % ASO, 3 | | |
| | Wt. % H/C, 7 | | |
| | Pressure and temperature | 155 | 90 |
| (44) | HF Stripper #2: | 200 | |
| | Top temperature | | 125 |
| | Bottom temperature | | 175 |
| (36) | Depropanizer: | 250 | |
| | Top temperature | | 130 |
| | Bottom temperature | | 200 |
| (46) | Liquid Separator | 220 | 100 |
| (23) | HF Stripper #1: | 120 | |
| | Top temperature | | 110 |
| | Bottom temperature | | 160 |
| (27) | Isostripper: | 115 | |
| | Top temperature | | 140 |
| | Bottom temperature | | 325 |

| Flow Rates and Compositions: | | | |
|---|---|---|---|
| (10) | Fresh Feed, B/D, | | 10,000 |
| | Component | Vol. % | |
| | Propane | 5 | |
| | Propylene | 4 | |
| | Isobutane | 46 | |
| | n-Butane | 12 | |
| | Butylenes | 33 | |
| (11') | Isobutane, B/D | | 22,000 |
| | (Vol. % iC$_4$ 95) | | |
| (38) | DC$_3$ Bottoms, B/D | | 3,050 |
| | (Vol. % iC$_4$ 98) | | |
| (37) | (33) Flow, B/D | | 16,800 |
| (14) | Hydrocarbon to Reactor, B/D | | 51,850 |
| (20) | Reactor Hydrocarbon Effluent, B/D | | 50,660 |
| | (Wt. % HF 1) | | |
| (24) | Bottoms from Stripper #1 (23), B/D | | 46,600 |
| | (HF nil) | | |
| (33) | Vapors from Separator (29), B/D | | (a)16,800 |
| | (HF nil) | | |
| (30) | Bottoms from Separator (29), B/D | | 29,800 |
| | (HF nil) | | |
| (51) | n-Butane Yield, B/D | | (a)1,200 |
| (54) | Alkylate Yield, B/D | | 6,600 |
| | RON Clear, 95 (estimated) | | |
| (25) | Vapor from HF Stripper #1 (23), B/D | | (b)3,500 |
| | (Wt. % HF 12.6) | | |
| (47) | HF Recycle, B/D | | 500 |
| (48) | Feed to HF Stripper #2 (44), B/D | | (c)3,550 |
| (50) | Bottoms from (44), B/D | | 3,550 |
| | (HF nil) | | |
| (49) | HF Overhead from (44), B/D | | (a) (e)10 |
| (35) | Total Feed to DC$_3$ (36), B/D | | (d)3,550 |
| (43) | DC$_3$ (36) Propane Yield, B/D | | 500 |
| (37) | To line 38, B/D | | 16,800 |
| (38') | [37 + 38], B/D | | 19,850 |

(a)Vapor, reported as liquid equivalent
(b)Vapor, reported as liquid, not including 510 B/D HF
(c)Not including 10 B/D HF
(d)With high propylene, stream 33 blends with stream 50 and is liquid-vapor mixture
(e)Contains hydrocarbon vapor, not shown

We claim:
1. An alkylation process which comprises:
 (a) reacting in a reaction zone at least one isoparaffin with at least one olefin in the presence of a sufficient amount of an HF acid catalyst at liquid phase conditions and for a period of time sufficient to form alkylate;
 (b) separating the alkylation reaction effluent from (a) into a liquid HF acid phase and a liquid hydrocarbon phase containing residual HF acid;
 (c) passing said liquid hydrocarbon phase to an HF stripping zone and subjecting same to stripping conditions sufficient to substantially remove HF and light hydrocarbons overhead and a hydrocarbon stream substantially free of HF as bottoms;

(d) vaporizing a portion of said bottoms obtained in step (c) and separating same into a vaporous hydrocarbon stream and a liquid hydrocarbon stream;

(e) fractionating said liquid hydrocarbon stream obtained in (d) into an isoparaffin stream, a normal paraffin stream and an alkylate stream;

(f) pressurizing said vaporous hydrocarbon stream separated in (d) and subjecting said pressurized stream to fractionation conditions and withdrawing propane overhead and isoparaffin as bottoms;

(g) condensing said overhead in (c) and separating same into a liquid HF acid catalyst phase and an HF-containing light hydrocarbon phase; and (h) stripping HF from said hydrocarbon phase separated in (g) in a second HF stripping zone under conditions sufficient to substantially remove HF overhead and an HF-free hydrocarbon stream comprising propane and isoparaffin as bottoms which is passed as part of the feed to fractionation in (f).

2. A process according to claim 1 wherein the bottoms stream in (c) is first indirectly heat exchanged with said liquid hydrocarbon phase in (c) being passed to said HF stripping and then HF acid being recycled to reaction in (a).

3. A process according to claim 1 wherein the isoparaffin streams separated in (e) and (f) are returned to (a) and (b) and liquid acid catalyst stream separated in (g) and vaporous acid stream separated in (h) are returned to said separating in (b).

4. A process according to claim 1 wherein the feed to (a) comprises isobutane, butylenes and HF acid.

5. A process according to claim 1 wherein at least a portion of said pressurized stream in (f) is passed with the bottoms removed from said second HF stripping and returned as a combined stream with other isoparaffins to (a) when propylene content in the pressurized stream is low.

6. In a process of alkylating at least one isoparaffinic hydrocarbon with at least one olefinic hydrocarbon in the presence of HF acid catalyst in a reaction zone and wherein the reaction mixture is separated into a liquid hydrocarbon phase and an HF acid catalyst phase and the separated hydrocarbon phase is subjected to separation of propane, HF acid, isoparaffins and paraffins from alkylate product, the improvement comprising:

(a) stripping HF acid from said hydrocarbon phase and vaporizing the stripped hydrocarbon phase;

(b) separating the vaporized, stripped hydrocarbon phase into a vapor phase and a liquid phase;

(c) increasing the pressure of said vapor phase in (b) and fractionating propane therefrom;

(d) recovering a liquid phase from (c) and returning same to alkylation; and (e) fractionating the liquid phase of (b) into a paraffin stream, an isoparaffin stream, and alkylate.

7. A process according to claim 6 further comprising the steps of:

(f) heat exchanging indirectly said liquid phase in (b) with recycle hydrocarbon streams and alkylate product stream within the system, and (g) condensing stripped HF acid in (a), passing non-condensed materials to a second HF stripping zone, recovering an HF-free stripped hydrocarbon stream which is passed to fractionation in (c).

8. A process according to claim 6 wherein the feed to the alkylation comprises mixed olefins of propylene and butylenes and the isoparaffin is isobutane.

* * * * *